United States Patent [19]
Miyauchi et al.

[11] Patent Number: 5,972,551
[45] Date of Patent: Oct. 26, 1999

[54] CRYSTALLINE TITANYL PHTHALOCYANINES AND USE THEREOF

[75] Inventors: Masato Miyauchi, Nara; Kaori Dakeshita; Ichiro Fujii, both of Gose, all of Japan

[73] Assignee: Sharp Kabushiki Kaisha, Japan

[21] Appl. No.: 08/995,397

[22] Filed: Dec. 19, 1997

[30] Foreign Application Priority Data

Dec. 26, 1996 [JP] Japan ................................ 8-347049
Aug. 1, 1997 [JP] Japan ................................ 9-207478

[51] Int. Cl.$^6$ ............................ G03G 5/06; C09B 67/50
[52] U.S. Cl. ............................ 430/78; 430/58; 430/100; 540/141
[58] Field of Search ................ 430/78, 100; 540/140, 540/141

[56] References Cited

U.S. PATENT DOCUMENTS

| | | | |
|---|---|---|---|
| 5,114,815 | 5/1992 | Oda et al. | 430/58 |
| 5,166,339 | 11/1992 | Duff et al. | 540/140 |
| 5,190,839 | 3/1993 | Fujimaki et al. | 540/141 |
| 5,350,655 | 9/1994 | Oshiba et al. | 430/78 |
| 5,512,674 | 4/1996 | Nukada et al. | 540/141 |
| 5,523,189 | 6/1996 | Molaire | 430/78 |
| 5,593,805 | 1/1997 | Go et al. | 430/78 |
| 5,736,282 | 4/1998 | Tamura et al. | 430/78 |

FOREIGN PATENT DOCUMENTS

| | | |
|---|---|---|
| 0404131 | 12/1990 | European Pat. Off. . |
| 0715216 | 6/1996 | European Pat. Off. . |
| 59-49544 | 3/1984 | Japan . |
| 60-86551 | 5/1985 | Japan . |
| 61-217050 | 9/1986 | Japan . |
| 61-239248 | 10/1986 | Japan . |
| 62-67094 | 3/1987 | Japan . |
| 63-20365 | 1/1988 | Japan . |
| 63-366 | 1/1988 | Japan . |
| 63-133462 | 6/1988 | Japan . |
| 63-198067 | 8/1988 | Japan . |
| 1-17066 | 1/1989 | Japan . |
| 2-8256 | 1/1990 | Japan . |
| 03033855 | 2/1991 | Japan . |
| 03033860 | 2/1991 | Japan . |
| 03033862 | 2/1991 | Japan . |
| 3-54264 | 3/1991 | Japan . |
| 3-54265 | 3/1991 | Japan . |
| 3-128973 | 5/1991 | Japan . |
| 04174442 | 6/1992 | Japan . |

OTHER PUBLICATIONS

Document: H. Mi\yazaki, "Photoreceptors for digital electrophotography", *Electrophotographics conference Journal*, vol. 32, No. 3, pp. 282–289 (1993).

Document: Frank H. Moser, et al., "Phthalocyanine Compounds", pp. 104–141 (1963).

Manabu Sawada: Dyes and Chemical Agents, vol. 24, No. 6, p. 122 (1997).

Oka et al, Journal of Imaging Science and Technology, "Study of the Relationship . . . Phthalocyanine Pigments", vol. 37, No. 6, pp. 607–609 (1993).

*Primary Examiner*—Roland Martin
*Attorney, Agent, or Firm*—Nixon & Vanderhye

[57] ABSTRACT

A crystalline titanyl phthalocyanine having diffraction peaks at least at 7.4°, 9.4°, 9.7° and 27.3° of Bragg angle (2θ±0.2°) in X-ray diffraction pattern with a doublet peak at 9.4° or 9.7°, one of the diffraction peaks at 9.4° and 9.7° being the maximum.

5 Claims, 5 Drawing Sheets

CRYSTALLINE TITANYL PHTHALOCYANINES AND USE THEREOF

CROSS-REFERENCE TO RELATED APPLICATIONS

This application is related to Japanese applications No. Hei 8(1996)-347049, filed on 26 Dec. 1996 and No. Hei 9(1997)-207478, filed on 1 Aug. 1997 whose priority is claimed under 35 USC § 119, the disclosure of which is incorporated by reference in its entirety.

BACKGROUND OF THE INVENTION

1. Field of the Invention

The present invention relates to a crystalline titanyl phthalocyanine and use thereof. More precisely, it relates to a titanyl phthalocyanine having a specific crystal form; to an electrophotographic photoconductor, in which the titanyl phthalocyanine is used as an electric charge generation material for use in printers, copying machines and the like and which is highly sensitive in wavelength range of near infrared rays; and to an image printing method using the photoconductor.

2. Description of the Prior Art

The electrophotographic photoconductors, which have now been in practical use, are classified into inorganic photoconductors using inorganic materials and organic photoconductors using organic materials.

Conventionally, as the electrophotographic photoconductor, inorganic materials have been mainly used because of their high sensitivity and good durability. Representative examples of the inorganic photoconductors are those of a selenium type made of amorphous selenium (a-Se), amorphous selenium arsenic (a-AsSe) and the like; those in which zinc oxide (ZnO) or cadmium sulfide (CdS) sensitized with dyes is dispersed in a binding resin; and those made of amorphous silicon (a-Si). However, among the above-mentioned inorganic photoconductors, the selenium-type photoconductors and the CdS-containing photoconductors are poor in heat resistance and stability upon storage. In addition to that, since they are toxic and cause environmental pollution, a question arises as to how they should be discarded. Since the photoconductors containing ZnO dispersed in resin have weak sensitivity and poor durability, they are now scarcely used. Though the a-Si-type photoconductor, which is drawing public attention as a pollution-free inorganic photoconductor, has advantages such as high sensitivity and high durability, it has disadvantages such as image defects resulting from its manufacturing process using a plasma CVD method and rising costs resulting from its poor productivity. As mentioned above, the inorganic photoconductors have various disadvantages.

On the other hand, with respect to organic photoconductors, there are many kinds of organic materials themselves. Therefore, by selecting a proper organic material, it is possible to manufacture an organic photoconductor having good stability upon storage and being free of toxicity. Moreover, the organic photoconductors can be manufactured at a low cost, because it is easy to form thin layers by coating. Therefore, the organic photoconductors have been studied eagerly, so that recently they are extremely improved in sensitivity and durability and are utilized in practical use with respect to the bis-azo-type compounds. So, nowadays, except in the special cases, organic materials are used as electrophotographic photoconductors.

In recent years, laser beam printers are widespread in which laser light is used as a light source in place of conventional white light and which have advantages such as fast printing, high image quality and non-impacting. For such printers, there has been a longing for development of photoconductors which may meet these demands. For laser light, a semiconductor laser, which is very compact and highly reliable, is especially used as the light source. Because the wavelength of the semiconductor laser light source is around 800 nm, there has been a longing for conductors having highly sensitive properties to the light of long wavelength around 800 nm.

However, because the known bis-azo compounds which have been conventionally in practical use are much sensitive to short wavelength range and middle wavelength range but less sensitive in long wavelength range, they are hardly applicable for practical use in the case of semiconductor laser light source. As other examples of organic materials which are relatively much sensitive in long wavelength range, stearic acid methine dyes, indoline dyes, cyanine dyes, pyrylium dyes and the like are known. However, none of them show stability in practical use (properties for repetitive use) and none can be applied for the practical devices actually.

On the other hand, a phthalocyanine compound has also been known as being much sensitive in long wavelength range. Since the phthalocyanine compound is relatively more stable than the above-mentioned dyes in practical use, it has been recently studied eagerly. With respect to the phthalocyanine compound, it has been known that the sensitivity peaks and physical properties of the phthalocyanine compound not only vary depending on whether or not a metal is present in its center and what kind of metal is present in its center but also vary depending on its crystal form (Manabu SAWADA: *Dyes and Chemical Agents*, vol. 24, No. 6, page 122(1997)). Therefore, it is important to develop photoconductors through the investigation of its crystal form as well. For example, there are some reports in which phthlocyanine having specific crystal form is selected for the electrophotographic photoconductor. For example, photoconductors made of non-metal phthalocyanine (e.g., Japanese Unexamined Patent Publication (Kokai) No. Sho 60(1985)-86551), photoconductors made of phthalocyanine containing aluminum (e.g., Japanese Unexamined Patent Publication No. Sho 63(1988)-133462) and photoconductors made of phthlocyanine containing a metal selected from titanium (e.g., Japanese Unexamined Patent Publication No. Sho 59(1984)-49544), indium, gallium or the like at the center thereof are known. In most of the cases, phthalocyanine of specific crystal form is selected.

Recently, there has been an eager study on titanyl phthalocyanines which are highly sensitive among these phthalocyanine compounds. Even titanyl phthalocyanine themselves are classified into many crystal forms in accordance with the difference in diffraction angle of X-ray diffraction pattern spectrum as shown in *Electrophotographics Conference Journal*, vol. 32, No. 3, p.282. More definitely, specific examples of the disclosed crystal type are α-type crystal (in Japanese Unexamined Patent Publications No. Sho 61(1986)-217050 and No. Sho 61(1986)-239248), A-type crystal (in Japanese Unexamined Patent Publication No. Sho 62(1987)-67094), C-type crystal (in Japanese Unexamined Patent Publications No. Sho 63(1988)-366 and No. Sho 63(1988)-198067), Y-type crystal (in Japanese Unexamined Patent Publications No. Sho 63(1988)-20365, No. Hei 02(1990)-8256, and No. Hei 01(1989)-17066), M-type crystal (in Japanese Unexamined Patent Publication No. Hei 03(1991)-54265), M-α-type crystal (in Japanese Unexamined Patent Publication No. Hei 03(1991)-54264), and I-type crystal (in Japanese Unexamined Patent Publication No. Hei 03(1991)-128973). In Japanese Unexamined Patent Publication No. Sho 62(1987)-67094, I-type and II-type crystals are disclosed. With respect to the crystals of titanyl phthalocyanine, crystals whose lattice constants are known from the structural analysis are the C-type, phase I-type and phase II-type crystals. Phase II-type crystal belongs to the triclinic crystal form and the phase I-type and C-type crystals belong to the monoclinic crystal form. When the crystal types disclosed in the specifications of the above-mentioned patent publications are analyzed on the basis of the known crystal lattice constants, it is found that the A-type and I-type crystals belong to phase I-type; the α-type and B-type crystals belong to phase II-type; and the M-type crystal belongs to C-type (similar explanation is found in *J. of Imaging Science and Technology*, vol. 37, No. 6, 1993, pp. 605–609).

However, there are some problems such that these types of titanyl phthalocyanines are still less sensitive and less stable in electric potential under repeated use. When the electrophotographic process using inverse developing is carried out using titanyl phthalocyanines, fogs tend to be formed on the resulting pictures (black spots tend to show up in the white background). Moreover, because its charging properties are not enough, sufficient image density can hardly be obtained.

As mentioned above, phthalocyanine compounds can be cited as organic compounds having sensitivity in long wavelength range. However, the phthalocyanine compounds themselves are not satisfactorily applicable for the electrophotographic photoconductors.

SUMMARY OF THE INVENTION

Thus, the present invention provides a crystalline titanyl phthalocyanine having diffraction peaks at least at 7.4°, 9.4°, 9.7° and 27.3° of Bragg angle (2θ±0.2°) in X-ray diffraction pattern with a doublet peak at 9.4° and 9.7°, one of the diffraction peaks at 9.4° and 9.7° being the maximum.

The present invention also provides an electrophotographic photoconductor containing the crystalline titanyl phthalocyanine as an electric charge generation material.

The present invention also provides an image printing method comprising charging the electrophotographic photoconductor and conducting reversal development to form printed images.

DESCRIPTION OF THE PREFERRED EMBODIMENTS

Figure 1:
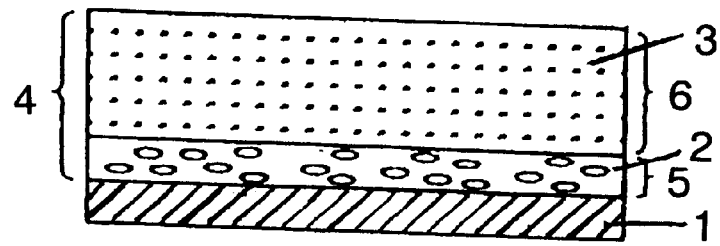
FIG. 1 shows a schematic view of layer structure of an electrophotographic photoconductor in accordance with the present invention, illustrating a sectional view of multi-layer type photoconductor wherein a photosensitive layer comprises two layers, i.e., an electric charge generation layer and an electric charge transport layer.

The crystalline titanyl phthalocyanine of the present invention has diffraction peaks at least at 7.4°, 9.4°, 9.7° and 23.7° of Bragg angle (2θ±0.2°) in X-ray diffraction pattern, the maximum diffraction peak is at 9.4° or 9.7°, and the diffraction peaks at 9.4° and 9.7° form a doublet peak. The titanyl phthalocyanine of the present invention is represented by the following structural formula (1):

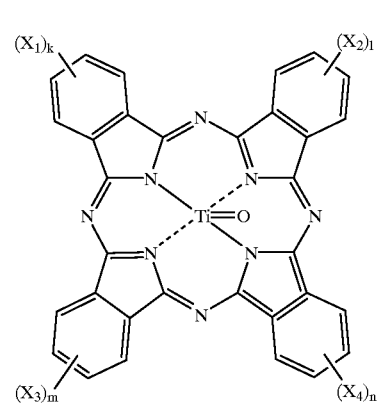

(1)

wherein $X_1$–$X_4$ are, the same or different, a hydrogen atom, a halogen atom, an alkyl group, an alkoxy group, a nitro group or a sulfonic group; k, l, m and n are, the same or different, an integer from 0 to 4.

Here, the halogen atom may be fluorine, chlorine, bromine or iodine; the alkyl group may be a straight-chain or branched-chain alkyl group having 1–5 carbon atom(s), for example, methyl, ethyl, propyl, isopropyl, butyl, isobutyl or the like; the alkoxy group may be a straight-chain or branched-chain alkoxy group having 1–5 carbon atom(s), for example, methoxy, ethoxy, propoxy, butoxy, isopropoxy, isobutoxy, sec-butoxy, tert-butoxy or the like.

For methods of preparing titanyl phthalocyanine of the present invention, any known method as described in "*Phthalocyanine Compounds*" by Moser and Thomas or the like can be used. For example, titanium phthalocyanine dichloride can be obtained in good yield by heating a mixture of o-phthalonitrile (1,2-dicyanobenzene) and titanium tetrachloride (titanium(IV) chloride) in an organic solvent like α-chloronaphthalene (1-chloronaphthalene), by heat-fusing them, or by heating a mixture of 1,3-diiminoisoindoline and tetrabutoxy titanium (titanium(IV) butoxide) in an organic solvent such as N-methylpyrrolidone or the like. Then, titanium phthalocyanine dichloride is hydrolyzed with a base or water to obtain titanyl phthalocyanine. The phenyl ring(s) in the titanyl phthalocyanine may be substituted by chlorine, fluorine, nitro group, cyano group or sulfonic group.

Such titanyl phthalocyanine may be treated with a hydrophobic organic solvent like halocarbon solvents such as dichloromethane, 1,2-dichloroethane; esters such as ethyl acetate, butyl acetate; ethers such as ethylether, methyethylether, diethylether, diisopropylether; aromatic hydrocarbons such as benzene, toluene, xylene, in the presence of water, thereby providing the crystalline titanyl phthalocyanine of the present invention.

For the way of treating the titanyl phthalocyanine with the hydrophobic organic solvent in the presence of water, there are a way such as swelling titanyl phthalocyanine with water followed by treating with the organic solvent, a way such as introducing powder of titanyl phthalocyanine into a mixture of the organic solvent and water without swelling and the like, to which however is not limited.

For the way of swelling titanyl phthalocyanine with water, there are a way such as dissolving titanyl phthalocyanine in sulfuric acid followed by precipating the titanyl phthalocyanine in wet paste form in water, a way such as swelling titanyl phthalocyanine with water in a stirring or dispersing equipment like homomixer, paintmixer, to which however ball mill, sand mill, etc., to which however is not limited.

Alternatively, the crystalline titanyl phthalocyanine of the present invention may be obtained as a result of mixing the titanyl phthalocyanine, which is obtained after the hydrolysis of the titanyl phthalocyanine dichloride, for a sufficient period of time, or of milling it with mechanical strain force.

As the apparatus used for mixing, there may be used conventional stirring apparatus, e.g., a homomixer, paintmixer, disperser, agitator or the like; and also for milling, there may be used a ball mill, sand mill, attritor, ultrasonic dispersing equipment or the like. After treatment, the resulting titanyl phthalocyanine may be filtered, washed with methanol, ethanol, water, etc. and isolated.

The titanyl phthalocyanine of the present invention includes not only the ones which are obtained by the above-mentioned methods but also any ones which are obtained by any other method but have the specific diffraction peaks of the present invention.

The titanyl phthalocyanine of the present invention shows excellent properties as the electric charge generation material for the electrophotographic photoconductor. In the present invention, other electric charge generation materials may be used together with the above-mentioned titanyl phthalocyanine. As such electric charge generation materials, there are α-type, β-type, Y-type or amorphous titanyl phthalocyanine which are different in crystal form from the titanyl phthalocyanine of the present invention and other types of phthalocyanines, azo-pigments, anthraquinone-pigments, perylene-pigments, polycyclic quinone-pigments, squaric-pigments or the like.

Figure 2:
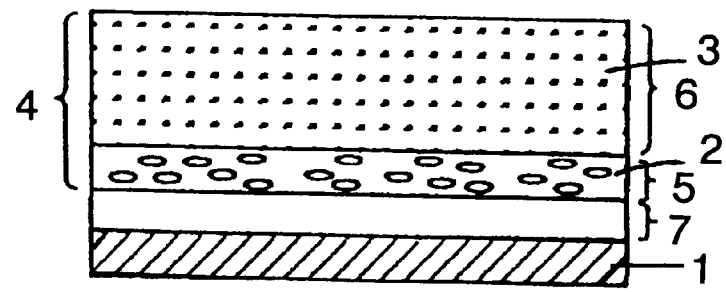
FIG. 2 shows a schematic view of layer structure of an electrophotographic photoconductor in accordance with the present invention, illustrating a sectional view of multi-layer type photoconductor wherein a photosensitive layer comprises three layers, i.e., an intermediate layer, an electric charge generation layer and an electric charge transport layer.
Figure 3:
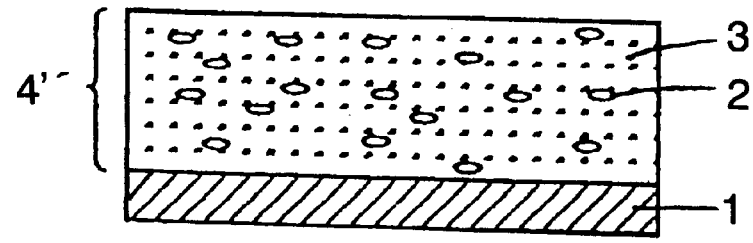
FIG. 3 shows a schematic view of layer structure of an electrophotographic photoconductor in accordance with the present invention, illustrating a sectional view of single-layer type photoconductor wherein an electric charge generation material is dispersed in an electric charge transport layer.
Figure 4:
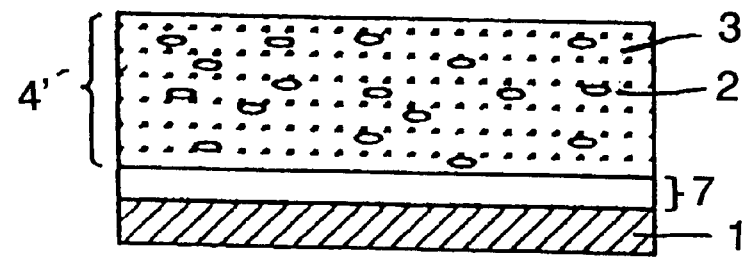
FIG. 4 shows a schematic view of layer structure of an electrophotographic photoconductor in accordance with the present invention, illustrating a sectional view of single-layer type photoconductor having an intermediate layer, wherein an electric charge generation material is dispersed in an electric charge transport layer.

The structure of the electrophotographic photoconductor of the present invention may be a separated function type photoconductor wherein a photosensitive layer comprises two layers, i.e., an electric charge generation layer and an electric charge transport layer as shown in FIG. 1; a single-layer type photoconductor wherein an electric charge generation material is dispersed in an electric charge transport layer as shown in FIG. 3; or a photoconductor wherein an undercoating layer as a known intermediate layer is placed between a conductive support and a photosensitive layer as shown in FIGS. 2 and 4.

As the conductive support to be used in the present invention, there may be used a substance which has conductivity itself such as aluminum, aluminum alloy, copper, zinc, stainless steel, nickel, titanium and the like. Also there may be used plastics or papers on which aluminum, gold, silver, copper, zinc, nickel, titanium, indium oxide, tin oxide or the like is vapor-deposited; plastics or paper which contains conductive particles; plastics which contains conductive polymer; and the like. Its shape may be a drum, sheet, seamless belt and the like.

In the case of the separated function type photoconductor, as an electric charge generation material in the electric charge generation layer, the titanyl phthalocyanine of the present invention can be used. Moreover, other electric charge generation materials as mentioned above may be contained in the electric charge generation layer. In this case, because the properties of the separated function type photoconductor are improved depending on the content of the titanyl phthalocyanine of the present invention, the more the content of the titanyl phthalocyanine in the charge generation layer is, the more it is preferred.

The electric charge generation layer may be formed by a deposition method such as vacuum vapor deposition or sputtering, chemical vapor deposition method. Alternatively, the electric charge generation material may be dissolved, or pulverized and dispersed by means of a ball mill, a sand grinder, a paint shaker, an ultrasonic disperser or the like, if necessary, followed by addition of a binding resin and a solvent thereto and forming the resultant into the charge generation layer by a baker applicator, a bar coater, casting method, spin coating method, etc. in the case of a sheet, or by a spray method, vertical ring method, dip coating method, etc. in the case of a drum.

The binding resin may be polyester resins, polyacrylates, polymethacrylate polyesters, polycarbonates, polyvinyl chlorides, polyvinyl acetates, polyvinyl acetoacetals, polyvinyl propionals, polyvinyl butyrals, phenoxy resins, epoxy resins, urethane resins, cellulose esters, cellulose ethers and the like, and copolymers thereof.

As the solvent, there may be used ketones such as acetone, methyl ethyl ketone, methyl isobutyl ketone, cyclohexanone and the like; esters such as ethyl acetate, butyl acetate and the like; ethers such as tetrahydrofuran, dioxane and the like; aromatic hydrocarbon such as benzene, toluene, xylene and the like; aprotic polar solvents such as N,N-dimethylformamide, dimethylsulfoxide and the like; which may be used alone or as a mixture thereof.

The thickness of the electric charge generation layer is preferably from 0.05 to 5 μm and more preferably from 0.08 to 1 μm.

As the electric charge transport material in the electric charge transport layer, there may be used high-molecular compounds such as polyvinyl carbazole, polysilane and the like and low-molecular compounds such as hydrazone compounds, pyrazoline compounds, oxadiazole compounds, stylbene compounds, triphenylmethane compounds, triphenylamine compounds, enamine compounds and the like.

The electric charge transport layer may be formed by dissolving an electric charge transport material in a solvent, then adding a binding resin thereto and forming the resultant mixture into the electric charge transport layer by a baker applicator, bar coater, casting method, spin coating method, etc. in the case of a sheet, or by a spray method, vertical ring method, dip coating method, etc. in the case of a drum.

As the binding resin, there may be used vinyl polymers such as polymethylmethacrylates, polystyrenes, polyvinyl chlorides, and the like, and a copolymer thereof; polycarbonates, polyesters, polyester carbonates, polysulfones, phenoxy resins, epoxy resins, silicone resins and the like. These may be used alone or as a mixture thereof. Also there may be used a copolymer of the monomers constituting the above-mentioned polymer, a partially crosslinked thermosetting resin or the like.

As the solvent, there may be used halocarbon solvents such as dichloromethane, 1,2-dichloroethane; ketones such as acetone, methyl ethyl ketone, cyclohexanone; esters such as ethyl acetate, butyl acetate; ethers such as tetrahydrofuran, dioxane; aromatic hydrocarbons such as benzene, toluene, xylene; aprotic polar solvents such as N,N-dimethylformamide, dimethyl sulfoxide; and the like.

The thickness of the electric charge transport layer is preferably from 5 to 60 $\mu$m, and more preferably 10 to 40 $\mu$m.

When needed, such additive as a leveling agent, an antioxidant, a sensitizing agent or the like may be contained in the electric charge generation layer or in the electric charge transport layer. As the antioxidant, there may be used $\alpha$-tocopherol, hydroquinone, hindered amines, hindered phenols, p-phenylenediamine, arylalkanes and derivatives thereof; organic sulfur compounds; organic phosphorus compounds; and the like.

As the intermediate layer which is placed between the conductive support and photosensitive layer, there may be used an inorganic layer (e.g., anodically oxidized aluminum film, aluminum oxide, aluminum hydroxide, titanium oxide and the like) or an organic layer of polyvinyl alcohol, polyvinyl butyral, polyvinyl pyrrolidone, polyacrylic acid, celluloses, gelatin, starch, polyurethane, polyimide, polyamide, casein, N-methoxymethylated nylons or the like. Furthermore, particles of titanium oxide, tin oxide, aluminum oxide and the like may be dispersed in the organic layer.

As an outermost surface, an overcoat layer of conventionally known thermoplastic or thermosetting polymer may be provided. Generally, the electric charge transport layer is formed on the electric charge generation layer. Alternatively, the electric charge generation layer may be formed on the electric charge transport layer. As a procedure to form each layer, known procedures are applicable such as successively applying the coating fluids obtained by dissolving or dispersing in a solvent the material to be contained within the layer.

In the case of single-layer type where the electric charge generation material is dispersed in the electric charge transport layer, the titanyl phthalocyanine compound of the present invention is dispersed in the electric charge transport layer in the above-mentioned content. Here, the particle size of the titanyl phthalocyanine needs to be sufficiently small, preferably 1 $\mu$m or less. If the amount of the electric charge generation material to be dispersed in the photosensitive layer is too small, the sensitivity is not enough. On the other hand, if the amount is excessive, an undesirable effect such as deterioration of charging properties and sensitivity is induced. Therefore, the amount of the electric charge generation material is preferably in the range of 0.5 to 50% by weight, and more preferably in the range of 1 to 20% by weight. The thickness of the photosensitive layer is preferably in the range of 5 to 50 $\mu$m, more preferably in the range of 10 to 40 $\mu$m. In this case, known plasticizers to improve layer-forming property, flexibility and mechanical strength, additives to suppress increase of the residual potential, co-dispersants to improve the stability of dispersion, leveling agents to improve coating properties, surface-active agents like silicone oil or fluorine-containing oil, other additives and the like may also be added.

Through the above procedures, the electrophotographic photoconductor can be obtained, which is sensitive to long wavelength light and particularly suitable for semiconductor lasers and LEDs, because the maximum sensitivity wavelength of the titanyl phthalocyanine lies around 817±0.5 nm.

The crystal of the titanyl phthalocyanine in the present invention is extremely stable and is superior in crystal stability against solvents, heat and mechanical strain. Moreover, the electrophotographic photoconductor formed of the titanyl phthalocyanine has characteristically superior sensitivity, charging properties and electric potential stability. These characteristics as mentioned above are great advantages not only in preparation of the present titanyl phthalocyanine, but also in preparation of the electrophotographic photoconductor and its use.

EXAMPLES

In order to describe the present invention in detail, Examples according to the present invention now follow, but are not limited thereto.

Manufacturing Example 1

The mixture of 40 g of o-phthalodinitrile (1,2-dicyanobenzene) and 18 g of titanium tetrachloride (titanium (IV) chloride) in 500 ml of $\alpha$-chloronaphthalene (1-chloronaphthalene) was stirred and heated at 200 to 250° C. for 3 hours in the atmosphere of nitrogen. After cooling to the temperature between 100 to 130° C., the mixture was filtered while it was hot. The residue was washed with 200 ml of $\alpha$-chloronaphthalene heated at 100° C. to give crude titanium phthalocyanine dichloride. The obtained crude product was washed with 200 ml of $\alpha$-chloronaphthalene and then with 200 ml of methanol at room temperature. And the suspension of the product in 500 ml of methanol was heated and washed for 1 hour. After the filtration, the obtained crude product was stirred and dissolved in 100 ml of conc. sulfuric acid followed by filtering insoluble fractions off. The crystal, which was precipitated by pouring the sulfuric acid solution into 3000 ml of water, was filtered. Heating and washing of the filtered crystal in 500 ml of water were repeated until pH of the solvent was 6 to 7. After the heating and washing, the crystal was filtered again. The obtained wet caky crystal was treated with dichloromethane, washed with methanol and dried to obtain the crystal of the present invention.

Figure 5:
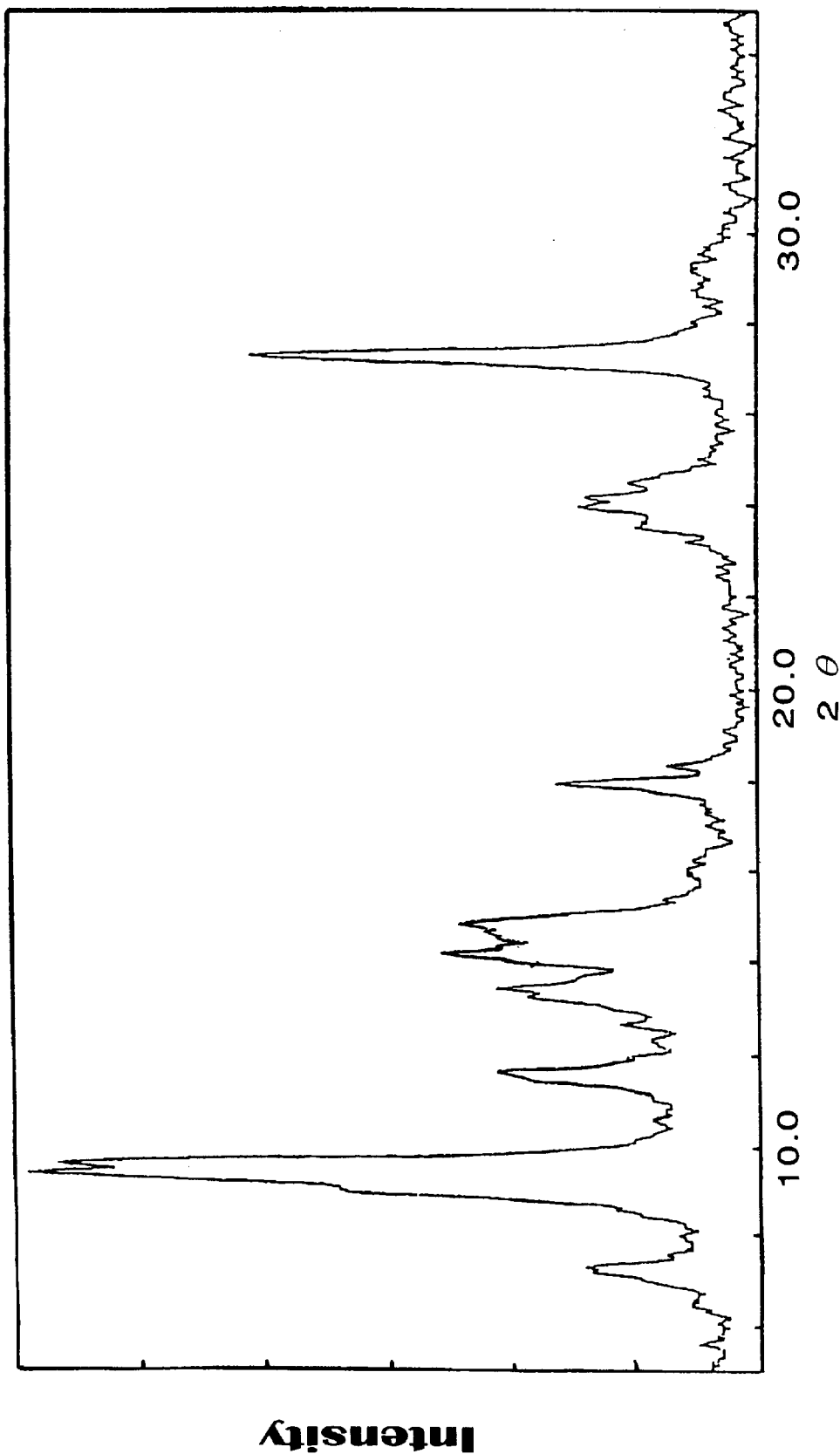
FIG. 5 shows a graphic representation showing an X-ray diffraction pattern of titanyl phthalocyanine obtained in Manufacturing Example 1 of the present invention.

This crystal shows an X-ray diffraction pattern shown in FIG. 5. According to this X-ray diffraction pattern, it is found that this crystal is the crystalline titanyl phthalocyanine of the present invention, which has the maximum diffraction peak at 9.4° of Bragg angle (2θ±0.2°) and other diffraction peaks at 7.4°, 9.7° and 27.3°. The diffraction peaks at 9.4° and 9.7° form a doublet peak.

The X-ray diffraction pattern was obtained under the condition mentioned below.

| | |
|---|---|
| X-ray source | CuKa = 1.54050 Å |
| voltage | 30 kV |
| current | 50 mA |

-continued

| | |
|---|---|
| start angle | 5.0 deg. |
| stop angle | 35.0 deg. |
| step angle | 0.01 deg. |
| time for measurement | 1 deg./min. |
| way of measurement | θ/2θ scan method |

Comparative Manufacturing Example 1

The crude titanium phthalocyanine dichloride, which was obtained by the same procedure as in Manufacturing Example 1, was washed with 200 ml of α-chloronaphthalene and then 200 ml of methanol at room temperature. And the suspension of the product in 500 ml of methanol was heated and washed for 1 hour. After filtration of the product, heating and washing the obtained crude product in 500 ml of water was repeated until pH of the solvent was 6 to 7. After the heating and washing, the solution was dried to obtain the crystal of Comparative Manufacturing Example 1.

Figure 8:
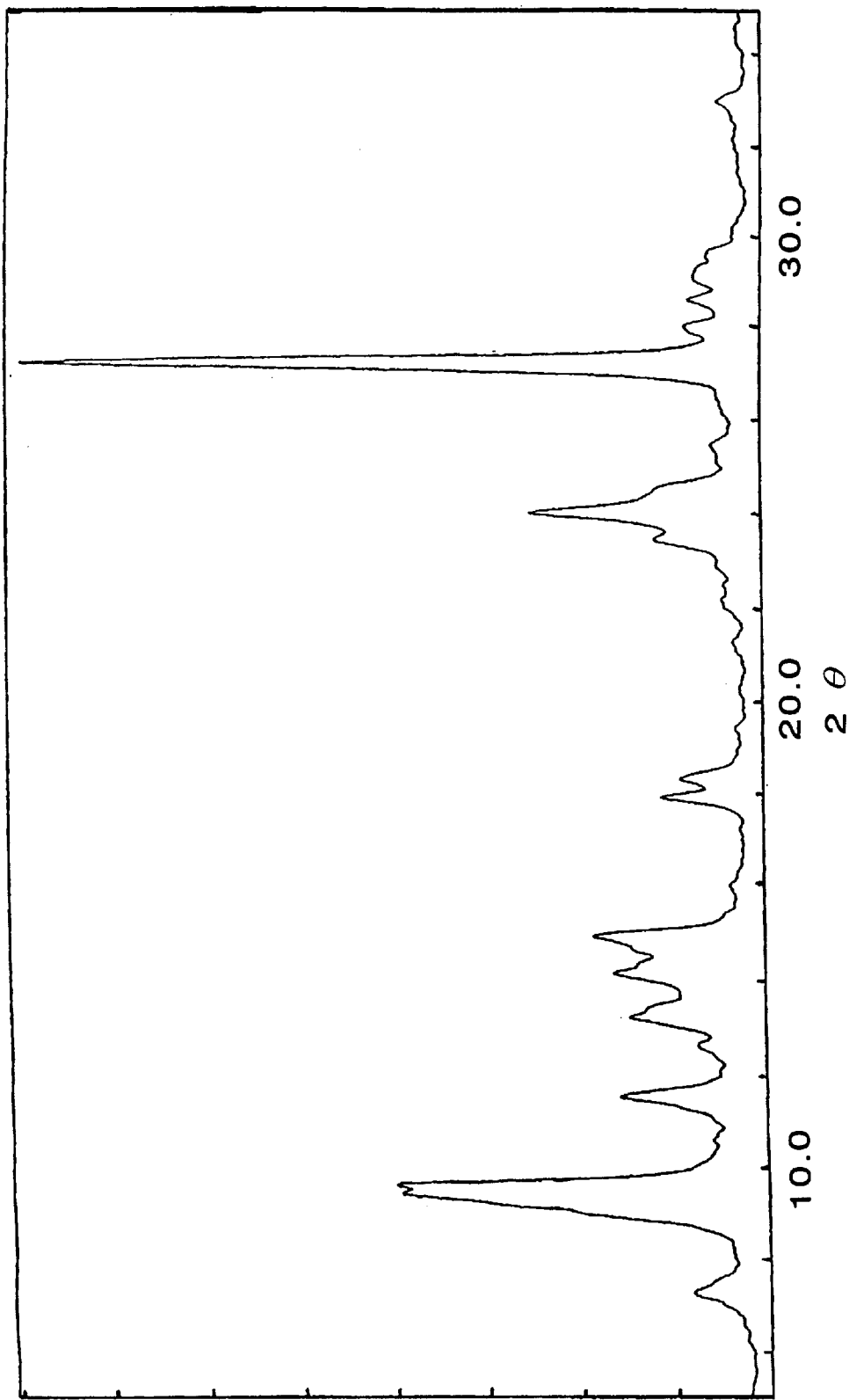
FIG. 8 shows a graphic representation showing an X-ray diffraction pattern of titanyl phthalocyanine obtained in Comparative Example 1.

This crystal shows an X-ray diffraction pattern shown in FIG. 8. The X-ray diffraction pattern was measured under the same condition as in Manufacturing Example 1. According to this X-ray diffraction pattern, it is found that this crystal is the crystalline titanyl phthalocyanine disclosed in Japanese Unexamined Patent Publication No. Hei 02(1990)-8256, which has the maximum diffraction peak at 27.3° of Bragg angle (2θ±0.2°) and other diffraction peaks at 7.4°, 9.7° and 24.2°.

Manufacturing Example 2

Crystalline titanyl phthalocyanine, which was obtained in Comparative Manufacturing Example 1, was mixed with tetrahydrofuran, treated for milling with 2 mm diameter glass beads by a paint conditioner equipment (manufactured by Red Level Co. ), washed with methanol and dried to obtain the crystal of the present invention.

Figure 6:
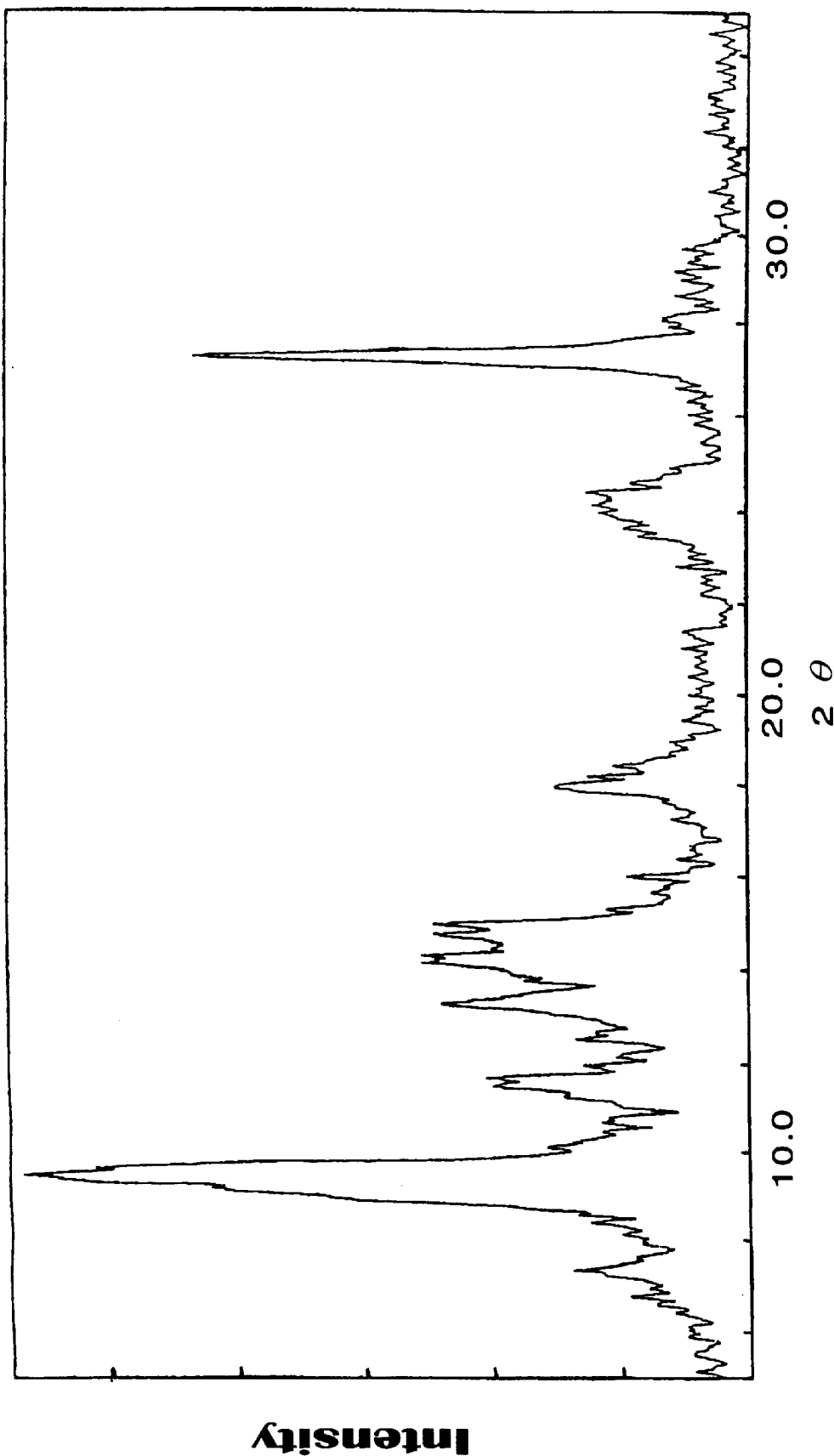
FIG. 6 shows a graphic representation showing an X-ray diffraction pattern of titanyl phthalocyanine obtained in Manufacturing Example 2 of the present invention.

This crystal shows an X-ray diffraction pattern shown in FIG. 6, which is similar to that in Manufacturing Example 1. According to this X-ray diffraction pattern, it is found that this crystal is the crystalline titanyl phthalocyanine of the present invention, which has the maximum diffraction peak at 9.4° of Bragg angle (2θ±0.2°) and other diffraction peaks at 7.4°, 9.7° and 27.3°. The diffraction peaks at 9.4° and 9.7° form a doublet peak.

Manufacturing Example 3

The crystalline titanyl phthalocyanine, which was obtained in Comparative Manufacturing Example 1, was mixed with methyl ethyl ketone, treated for milling with 2 mm diameter glass beads by the paint conditioner equipment (Red Level Co. ), washed with methanol and dried to obtain the crystal of the present invention.

Figure 7:
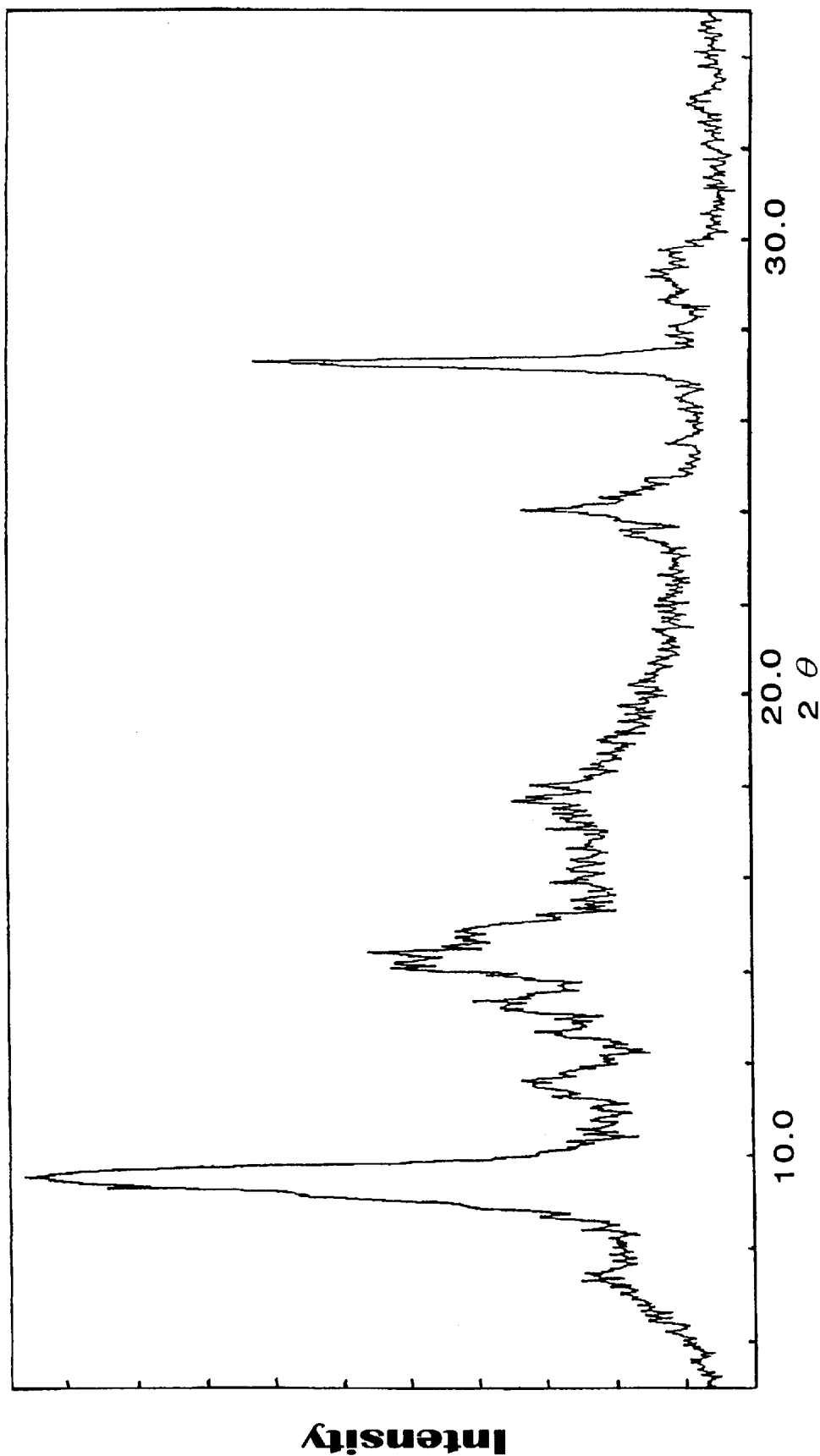
FIG. 7 shows a graphic representation showing an X-ray diffraction pattern of titanyl phthalocyanine obtained in Manufacturing Example 3 of the present invention.

According to this X-ray diffraction pattern, it is found that this crystal is the crystalline titanyl phthalocyanine of the present invention, which has the maximum diffraction peak at 9.7° of Bragg angle (2θ±0.2°) and other diffraction peaks at 7.4°, 9.4° and 27.3° shown in FIG. 7. The diffraction peaks at 9.7° and 9.4° form a doublet peak.

Example 1

On a polyester film with vapor-deposited aluminum as a conductive support, the solution of 6 parts by weight of nylon copolymer (manufactured by Toray Industries, Inc.: CM8000) dissolved in a mixed solvent of 47 parts by weight of methanol and 47 parts by weight of chloroform was applied, followed by drying to provide the intermediate layer of 1 μm in thickness.

One part by weight of the crystalline titanyl phthalocyanine of the present invention obtained in Manufacturing Example 1 and 1 part by weight of polyvinyl butyral (manufactured by Sekisui Chemical Co., Ltd.: ESLEC BX-1 (POLYVINYL BUTYRAL)) were mixed with 70 parts by weight of tetrahydrofuran, followed by dispersing-treatment together with 2 mm diameter glass beads in a paint conditioner equipment (manufactured by Red Level Co.). The obtained solution was applied on the above-mentioned intermediate layer, followed by drying to provide the electric charge generation layer of 0.4 μm in thickness.

Then, an enamine compound having the following chemical formula (2) and a polycarbonate resin (manufactured by Mitsubishi Gas Chemical Company, Inc.: PCZ-200) in a weight ratio of 1:1 were mixed in dichloromethane as a solvent to prepare 15 wt % solution. This solution was applied on the above-mentioned electric charge generation layer, followed by drying to provide the electric charge transport layer of 25 μm in thickness.

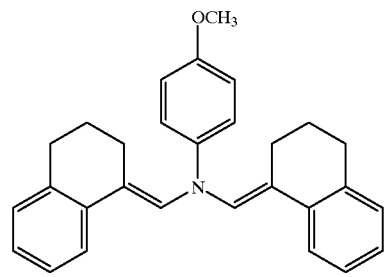

(2)

In the above-mentioned manner, the multi-layer type photoconductor sample 1 was obtained which was constructed with the electric charge generation layer and the electric charge transport layer.

Example 2

On a polyester film with vapor-deposited aluminum as a conductive support, the solution obtained by the dispersing treatment in Example 1 was directly applied, followed by drying to provide the electric charge generation layer of 0.4 μm in thickness. Then, on the electric charge generation layer, an electric charge transport layer was formed by using the butadiene compound having the following chemical formula (3) as an electric charge transport material. Thus, the multi-layer type photoconductor sample 2, which was similar to the one in Example 1, was obtained.

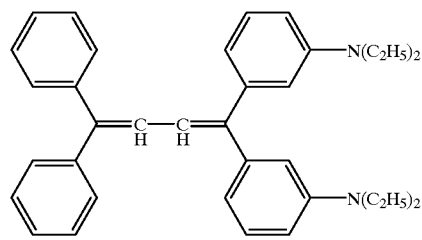

(3)

Example 3

A multi-layer type photoconductor sample 3, which was similar to the one obtained in Example 1, was obtained in the same manner as in Example 1 except that as a resin for the electric charge generation layer, vinyl chloride-vinyl acetate copolymer resin (manufactured by Sekisui Chemical Co., Ltd.: ESLEC M-1) was used and as an electric charge transport material, a hydrazone compound having the following chemical formula (4) was used.

(4)

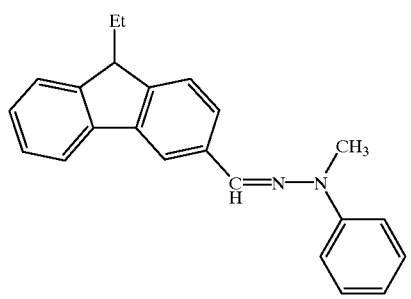

Example 4

On a polyester film with vapor-deposited aluminum as the conductive support, the solution of 6 parts by weight of nylon copolymer (manufactured by Toray Industries, Inc.: CM8000) dissolved in a mixed solvent of 47 parts by weight of methanol and 47 parts by weight of chloroform, was applied, followed by drying to provide the intermediate layer of 1 μm in thickness.

One part by weight of the crystalline titanyl phthalocyanine of the present invention obtained in Manufacturing Example 2 and 1 part by weight of polyvinyl butyral (manufactured by Sekisui Chemical Co., Ltd.: ESLEC BL-1) were mixed with 70 parts by weight of cyclohexanone, followed by dispersing-treatment together with 2 mm diameter glass beads by the paint conditioner equipment (manufactured by Red Level Co.). The obtained solution was applied on the above-mentioned intermediate layer, followed by drying to provide the electric charge generation layer of 0.4 μm in thickness.

Then, an enamine compound having the above-mentioned chemical formula (2) and the polycarbonate resin (manufactured by Mitsubishi Gas Chemical Company, Inc.: PCZ-200) in a weight ratio of 1:1 were mixed in dichloromethane as a solvent to prepare 15 wt % solution. This solution was applied on the above-mentioned electric charge generation layer, followed by drying to provide the dry electric charge transport layer of 25 μm in thickness.

In the above-mentioned manner, the multi-layer type photoconductor sample 4 was obtained which was constructed with the electric charge generation layer and the electric charge transport layer.

Example 5

A multi-layer type photoconductor sample 5, which was similar to the one in Example 4, was constructed in the same manner as in Example 1 except that, as an electric charge transport material, a hydrazone compound having the above-mentioned chemical formula (4) was used.

Example 6

On a polyester film (100 μm of layer thickness) with vapor-deposited aluminum as the conductive support, a solution of 6 parts by weight of nylon copolymer (manufactured by Toray Industries, Inc.: CM8000) dissolved in a mixed solvent of 47 parts by weight of methanol and 47 parts by weight of chloroform, was applied, followed by drying to provide the intermediate layer of 1 μm in thickness.

One part by weight of the crystalline titanyl phthalocyanine of the present invention obtained in Manufacturing Example 1 and 10 parts by weight of an enamine compound having the above-mentioned chemical formula [2] were mixed with 10 parts by weight of polycarbonate resin (manufactured by Mitsubishi Gas Chemical Company, Inc.: PCZ-200) in dichloromethane as a solvent to prepare 15 wt % solution, to which glass beads of 2 mm diameter were dispersed by the paint conditioner equipment (manufactured by Red Level Co.).

The obtained dispersion was applied on the above-mentioned intermediate layer, followed by drying to provide the dry photosensitive layer of 25 μm in thickness.

In the above-mentioned manner, the single-layer type photoconductor layer 6 was thus obtained wherein the electric charge generation material was dispersed in the electric charge transport layer.

Example 7

On a polyester film with vapor-deposited aluminum as the conductive support, the solution of 6 parts by weight of nylon copolymer (manufactured by Toray Industries, Inc.: CM8000) dissolved in a mixed solvent of 47 parts by weight of methanol and 47 parts by weight of chloroform, was applied, followed by drying to provide the intermediate layer of 1 μm in thickness.

One part by weight of the crystalline titanyl phthalocyanine of the present invention obtained in Manufacturing Example 3 and 1 part by weight of polyvinyl butyral (manufactured by Sekisui Chemical Co., Ltd.: ESLEC BL-1) were mixed with 70 parts by weight of methylethylketone, followed by dispersing-treatment together with 2 mm diameter glass beads by the paint conditioner equipment (manufactured by Red Level Co.). The obtained dispersion was applied on the above-mentioned intermediate layer, followed by drying to provide the electric charge generation layer of 0.5 μm in thickness.

Then, an enamine compound having the above-mentioned chemical formula (2) and a polycarbonate resin (manufactured by Mitsubishi Gas Chemical Company, Inc.: S2000) in a weight ratio of 1:1 were mixed with dichloromethane as a solvent to prepare 15 wt solution. This solution was applied on the above-mentioned electric charge generation layer, followed by drying to provide the electric charge transport layer of 25 μm in thickness.

In the above-mentioned manner, the multi-layer type photoconductor sample 7 was thus obtained which was constructed with the electric charge generation layer and the electric charge transport layer.

Example 8

A multi-layer type photoconductor sample 8, which was similar to the one in Example 7, was constructed in the same manner as in Example 7 except that a hydrazone compound having the above-mentioned chemical formula (4) was used as the electric charge transport material.

Example 9

On a polyester film (100 μm of layer thickness) with vapor-deposited aluminum as the conductive support, the solution of 6 parts by weight of nylon copolymer (manufactured by Toray Industries, Inc.: CM8000) dissolved in a mixed solvent of 47 parts by weight of methanol and 47 parts by weight of chloroform, was applied, followed by drying to provide the intermediate layer of 1 µm in thickness.

One part by weight of the crystalline titanyl phthalocyanine of the present invention obtained in Manufacturing Example 3 and 10 part by weight of an enamine compound having the above-mentioned chemical formula (2) were mixed with 10 parts by weight of polycarbonate resin (manufactured by Mitsubishi Gas Chemical Company, Inc.: PCZ-200) in tetrahydrofuran as a solvent to prepare 15 wt % solution, to which glass beads of 2 mm diameter were dispersed by the paint conditioner equipment (manufactured by Red Level Co.).

By applying the thus obtained dispersion on the above-mentioned intermediate layer, the photosensitive layer of 25 µm in thickness was prepared.

The single-layer type photoconductor sample 9, wherein the electric charge generation material was dispersed in the electric charge transport layer, was thus obtained.

Comparative Example 1

By using the crystal of titanyl phthalocyanine having the same X-ray diffraction pattern as that shown in FIG. 8 of the Comparative Manufacturing Example 1, a multi-layer type photoconductor sample 7 was obtained which was similar to the one in Example 1.

Comparative Example 2

By using the crystal of titanyl phthalocyanine having the same X-ray diffraction pattern as that shown in FIG. 8 of the Comparative Manufacturing Example 1, a multi-layer type photoconductor sample 8 was obtained which was similar to the one in Example 2.

Samples 1 to 10 obtained in the above-mentioned Examples and Comparative Examples are shown in Table 1.

TABLE 1

|  | | electric charge generation material | electric charge transport material |
|---|---|---|---|
| Sample 1 | Example 1 | Manufacturing Example 1 | Formula (2) |
| Sample 2 | Example 2 | Manufacturing Example 1 | Formula (3) |
| Sample 3 | Example 3 | Manufacturing Example 1 | Formula (4) |
| Sample 4 | Example 4 | Manufacturing Example 2 | Formula (2) |
| Sample 5 | Example 5 | Manufacturing Example 2 | Formula (4) |
| Sample 6 | Example 6 | Manufacturing Example 1 | Formula (2) |
| Sample 7 | Example 7 | Manufacturing Example 3 | Formula (2) |
| Sample 8 | Example 8 | Manufacturing Example 3 | Formula (4) |
| Sample 9 | Example 9 | Manufacturing Example 3 | Formula (2) |
| Sample 10 | Comparative Example 1 | Comparative Manufacturing Example 1 | Formula (2) |
| Sample 11 | Comparative Example 2 | Comparative Manufacturing Example 1 | Formula (3) |

(Evaluation)

The electrophotographic characteristics of the thus prepared electrophotographic photoconductors were evaluated by means of an electrostatic recording paper test apparatus (manufactured by Kawaguchi Denki: EPA-8200). The measurement employed a condition in which an applied voltage was −6 kV and a static system was No. 3. An exposure light amount E1/2 ($\mu J/cm^2$) of the electrophotographic photoconductor required for reducing the potential from −500 V to −250 V by monochromatic light of 780 nm (irradiation light: 2 $\mu W/cm^2$) separated by spectroscopy with an interference filter and the initial potential VO (−volt) were measured. Also with respect to the single-layer type, the same electrostatic recording paper test apparatus was used and the measurement employed a condition that an applied voltage was +6 kV and a statistic system was No. 3. An exposure light amount E1/2 ($\mu J/cm^2$) of the electrophotographic photoconductor required for reducing the potential from +500 V to +250 V by monochromatic light of 780 nm (irradiation light: 10 $\mu W/cm^2$) separated by spectroscopy with an interference filter and the initial potential VO (+volt) were measured.

Non-copy aging was conducted for 10,000 times by a commercial digital copying machine (manufactured by Sharp Corporation: AR5040) which was reconstructed by using the photosensitive layer of Table 1 as a drum part. Before and after that process, VO and E1/2 were measured by means of the above-mentioned electrostatic recording paper test apparatus.

The results are shown in Table 2.

TABLE 2

|  | charging potential (VO) | | exposure light amount ($\mu J/cm^2$) for reduction to half | |
|---|---|---|---|---|
|  | Initial | After 10,000 copying | Initial | After 10,000 copying |
| Example 1 | −502 | −490 | 0.05 | 0.11 |
| Example 2 | −511 | −489 | 0.11 | 0.16 |
| Example 3 | −521 | −500 | 0.08 | 0.13 |
| Example 4 | −500 | −499 | 0.06 | 0.10 |
| Example 5 | −498 | −484 | 0.08 | 0.15 |
| Example 6 | +510 | +502 | 0.15 | 0.19 |
| Example 7 | −505 | −496 | 0.05 | 0.10 |
| Example 8 | −512 | −495 | 0.08 | 0.14 |
| Example 9 | +502 | +490 | 0.16 | 0.20 |
| Comparative Example 1 | −478 | −430 | 0.18 | 0.39 |
| Comparative Example 2 | −498 | −460 | 0.22 | 0.39 |

As is shown in Table 2, the deterioration of potential after the charging potential durability test (10,000 times) in any of the Examples 1 to 9 is sufficiently small compared with the conventional ones in Comparative Examples 1 and 2. Moreover, the initial sensitivity (exposure light amount for reduction to half) in any of the Examples 1 to 9 is sufficiently high compared with the ones in Comparative Examples and the deterioration of sensitivity in any of the Examples 1 to 9 is smaller even after the charging potential durability test.

Another example, which is applied for the reversal developing process, is explained hereinbelow.

Each photoconductor, which was prepared in Examples 1 to 9 and Comparative Examples 1 and 2, was mounted on a machine reconstructed from a commercial available digital copying machine (manufactured by Sharp Corporation: AR5040). Reverse developing was conducted for each machine with two-components type developing solution containing positive or negative toner for positive or negative charging, respectively. After 10,000 image printing, the image density and the amount of black spots in white background were determined in three grades of "○", "Δ" and "X" with respect to each material. The result is shown below in Table 3. In this case a semiconductor laser (780 nm) was used as the light source.

TABLE 3

|  | Image density | Amount of black spots in white background |
|---|---|---|
| Example 1 | ○ | ○ |
| Example 2 | Δ | Δ |
| Example 3 | Δ | ○ |
| Example 4 | ○ | ○ |
| Example 5 | ○ | Δ |
| Example 6 | Δ | Δ |
| Example 7 | ○ | ○ |
| Example 8 | ○ | Δ |
| Example 9 | Δ | Δ |
| Comparative Example 1 | X | X |
| Comparative Example 2 | X | X |

In Table 3, the amount of black spots is represented by:
○: one spot/cm² or less
Δ: 1 to 5 spots/cm²
X: 5 spots/cm² or more.

Image density was measured by means of Macbeth densitometer RD-918 type:
○: reflected density of 1.4 or more
Δ: reflected density of 1.3 to 1.4
X: reflected density of 1.3 or less.

According to the printing image method of the present invention, as shown above, higher image density and less amount of black spots can be obtained even after image printing conducted many times.

As is apparent hereinabove, the present invention provides the crystalline titanyl phthalocyanine which is highly sensitive in long wavelength range and highly durable, the electrophotographic photoconductor using the crystalline titanyl phthalocyanine, and the image printing method using the photoconductor. Accordingly, the crystalline titanyl phthalocyanine is suitable for photoconductors of laser printers and digital copying machines whose light source is a semiconductor laser which is recently under great development.

What is claimed is:

1. A crystalline titanyl phthalocyanine having diffraction peaks at least at 7.4°, 9.4°, 9.7° and 27.3° of Bragg angle (2θ±0.2°) in X-ray diffraction pattern with a doublet peak at 9.4° or 9.7°, one of the diffraction peaks at 9.4° and 9.7° being the maximum.

2. The crystalline titanyl phthalocyanine of claim 1, which is represented by the formula (1):

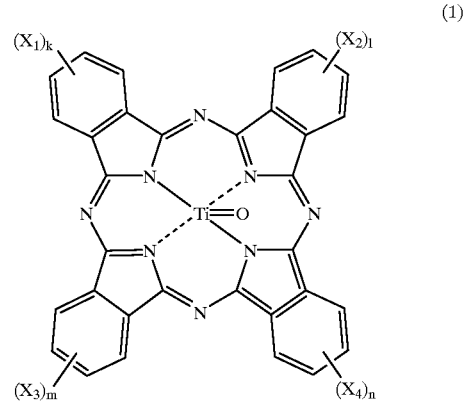

(1)

wherein $X_1$–$X_4$ are, the same or different, a hydrogen atom, a halogen atom, an alkyl group, an alkoxy group, a nitro group or a sulfonic group; k, l, m and n are, the same or different, an integer from 0 to 4.

3. The crystalline titanyl phthalocyanine of claim 2 wherein k, l, m and n are 0.

4. An electrophotographic photoconductor containing the crystalline titanyl phthalocyanine of claim 1 as an electric charge generation material.

5. An image printing method comprising charging the electrophotographic photoconductor of claim 4 and conducting reversal developing to form printed images.

* * * * *